(12) United States Patent
Karlsson et al.

(10) Patent No.: US 12,726,777 B2
(45) Date of Patent: Sep. 1, 2026

(54) ONE-PIECE COUPLING FOR A BONE ANCHORED HEARING SYSTEM

(71) Applicant: Oticon Medical A/S, Smørum (DK)

(72) Inventors: Martin Karlsson, Askim (SE); Vikram Shetty, Askim (SE)

(73) Assignee: OTICON MEDICAL A/S, Smørum (DK)

(*) Notice: Subject to any disclaimer, the term of this patent is extended or adjusted under 35 U.S.C. 154(b) by 413 days.

(21) Appl. No.: 18/490,778

(22) Filed: Oct. 20, 2023

(65) Prior Publication Data

US 2024/0147170 A1 May 2, 2024

(30) Foreign Application Priority Data

Oct. 27, 2022 (EP) .................................... 22204104

(51) Int. Cl.
*A61B 5/00* (2006.01)
*A61B 17/86* (2006.01)
*H04R 25/00* (2006.01)

(52) U.S. Cl.
CPC ....... *H04R 25/606* (2013.01); *A61B 17/8605* (2013.01); *H04R 2225/67* (2013.01); *H04R 2460/13* (2013.01)

(58) Field of Classification Search
CPC .............. H04R 25/606; H04R 2225/67; H04R 2460/13; A61B 17/8605
See application file for complete search history.

(56) References Cited

U.S. PATENT DOCUMENTS

| | | | | |
|---|---|---|---|---|
| 2005/0248158 | A1 | 11/2005 | Westerkull | |
| 2010/0292529 | A1* | 11/2010 | Westerkull ........... | H04R 25/606 600/25 |
| 2016/0100264 | A1 | 4/2016 | Jinton et al. | |
| 2018/0077505 | A1* | 3/2018 | Bern .................... | H04R 25/606 |
| 2021/0281960 | A1 | 9/2021 | Andersson | |

FOREIGN PATENT DOCUMENTS

| | | |
|---|---|---|
| SE | 467082 | 4/1991 |
| WO | 20210074682 | 4/2021 |

* cited by examiner

*Primary Examiner* — Joel F Brutus
(74) *Attorney, Agent, or Firm* — Birch, Stewart, Kolasch & Birch, LLP

(57) ABSTRACT

Embodiments of the present disclosure generally relates to a coupling for coupling an external hearing device with an abutment of a bone anchored hearing system. The disclosure more particularly relates to a coupling for coupling an external hearing device with an abutment of a bone anchored hearing system, the coupling including: at least two coupling arms for establishing a connection to the abutment of the bone anchored hearing system. The disclosure further relates to a coupling assembly for coupling an external hearing device with an abutment of a bone anchored hearing system and a bone anchored hearing system.

13 Claims, 6 Drawing Sheets

ONE-PIECE COUPLING FOR A BONE ANCHORED HEARING SYSTEM

FIELD

The present disclosure generally relates to a coupling for coupling an external hearing device with an abutment of a bone anchored hearing system. The disclosure more particularly relates to a coupling for coupling an external hearing device with an abutment of a bone anchored hearing system, the coupling comprising: at least two coupling arms for establishing a connection to the abutment of the bone anchored hearing system. The disclosure further relates to a coupling assembly for coupling an external hearing device with an abutment of a bone anchored hearing system and a bone anchored hearing system.

BACKGROUND

Bone anchored hearing systems are essential for rehabilitation of patients suffering from specific types of hearing loss for which traditional hearing aids are insufficient. This type of hearing system consists of an external hearing device comprising a vibrator which is connected via a coupling assembly to a percutaneous abutment mounted on an implant anchored in the skull bone.

The vibrator of the external hearing device transduces an electrical auditory signal into a mechanical stimulus perceivable by the user via bone conduction. The vibrator is a resonant system formed by an electromagnetically driven mass suspended by a vibrator spring. Depending on the chosen weight of the mass and the spring rate of the vibrator spring, the vibrator resonates at a specific peak frequency. Connected to the vibrator is the coupling assembly attachable to the percutaneous abutment mounted on the implant. The purpose of the coupling assembly is to transmit the vibrations into the skull without distortion. On top of that it should also facilitate easy removal and fitting during the products life.

In known coupling assemblies as shown in FIG. 1, the vibrator comprises a steel connector plate that has to be inserted from the inside of an external hearing device. This results in a large cut out in the hearing device housing which makes sealing between the vibrator and the housing difficult.

This problem is even more serious because the coupling assembly stack height is quite large. The coupling of the known coupling assembly comprises injection molded left and right coupling shoes as well as a coupling plug which have to be placed in the right order on to the connector plate of the vibrator and then held together tightly in place with a coupling spring. On top of that, the plurality of components comprising the coupling creates complex and sensitive tolerance chains for critical interfaces, which in turn requires difficult and expensive production control.

Therefore, there is a need to provide a solution that addresses at least some of the above-mentioned problems.

SUMMARY

According to a first aspect of the present disclosure, a coupling for coupling an external hearing device with an abutment of a bone anchored hearing system may be provided, i.e. a coupling for coupling an external hearing device of the bone anchored hearing system and the abutment of an implant of the bone anchored hearing system. The coupling may be configured to be disposed between the external hearing device and the abutment of the bone anchored hearing system. The coupling may be configured to transmit vibrations from the external hearing device of the bone anchored hearing system, in particular a vibrator of the external hearing device, to the abutment of the bone anchored hearing system. The coupling may further be configured to facilitate coupling and removal of the external hearing device to/from the abutment of the implant of the bone anchored hearing system.

The coupling may comprise at least two coupling arms for establishing a connection between the coupling and the abutment of the bone anchored hearing system. The at least two coupling arms of the coupling may be configured to at least partially engage the abutment of the bone anchored hearing system when the external hearing device is coupled to the abutment via the coupling assembly. It is conceivable that the at least two coupling arms can go inside the abutment wherein a coupling force is at least partly acting radially outwardly against the inside of the abutment.

It is also conceivable that the at least two coupling arms of the coupling can go on the outside of the abutment where a coupling force is at least partly acting radially inwardly against the outside of the abutment. Particularly, the at least two coupling arms of the coupling may be configured to at least partially embrace the abutment of the bone anchored hearing system when an external hearing device is coupled to the abutment via the coupling assembly.

The coupling may comprise exactly two coupling arms for establishing the connection between the coupling and the abutment of the bone anchored hearing system. It is also conceivable that the coupling may comprise e.g. four or six coupling arms for establishing the connection between the coupling and the abutment of the bone anchored hearing system. The coupling may comprise an even or uneven number of coupling arms. The arrangement of the coupling arms may be symmetrically or unsymmetrically. In particular, the coupling may comprise an even number of substantially identical coupling arms, with two arms facing each other in each case.

The coupling may be configured as a one-piece coupling. Instead of comprising multiple separate coupling parts such as coupling shoes and a coupling plug, the coupling of the first aspect of the present disclosure may thus be configured as a one-piece coupling comprising at least two coupling arms for establishing a connection to an abutment of a bone anchored hearing system. The at least two coupling arms may, for example, be attached to a coupling body connecting the at least two coupling arms.

The coupling of the present disclosure thus provides an efficient solution to the problems with current designs of couplings for bone anchored hearing systems. It has been found that the coupling according to the first aspect of the present disclosure significantly facilitates connecting an external hearing device with an abutment of a bone anchored hearing system as the number of parts is limited to just one component. This also facilitates manufacturing of the coupling, as no tolerances have to be observed with respect to other coupling parts. The coupling according to the first aspect of the present disclosure thus provides a simple and cost effective solution for coupling an external hearing device with an abutment of a bone anchored hearing system.

According to a second aspect of the present disclosure, a coupling assembly for coupling an external hearing device with an abutment of a bone anchored hearing system may comprise a coupling according to the first aspect. The coupling assembly may be configured to detachably attach the external hearing device of the bone anchored hearing system to the abutment of the bone anchored hearing system.

The coupling may be disposed between the external hearing device and the abutment of the bone anchored hearing system. The coupling assembly may further comprise a coupling spring for applying a force on the at least two coupling arms of the coupling against the abutment of the bone anchored hearing system when establishing a connection between the coupling and the abutment of the bone anchored hearing system. The coupling spring may be configured to control the strength of the coupling between the external hearing device and the abutment of the bone anchored hearing system. The coupling spring may be attached to the coupling, in particular the at least two coupling arms of the coupling, for applying the force on the at least two coupling arms.

Depending on the arrangement of the at least two coupling arms on the inside or the outside of the abutment, the coupling spring may either be configured to apply a force outwardly or to apply a force inwardly on the coupling arms against the abutment. In particular, the coupling spring may be configured to press the at least two coupling arms against the abutment. The strength of the coupling between the abutment and the external hearing device may be at least mainly controlled by the coupling spring, which preferably may be attached on the outside of the at least two coupling arms. The coupling spring may be a circular spring that presses the at least two coupling arms against the outside of the abutment. Preferably, the coupling assembly may be configured to provide a snap coupling when establishing a connection between an external hearing device and an abutment of a bone anchored system. This allows for a simple fixture and a simple removal of the external hearing device, which is particularly advantageous as coupling and de-coupling of the components may e.g. be performed on a daily basis. The coupling spring may e.g. comprise a C-clip spring, in particular a C-clip metal spring.

With the coupling assembly of the present disclosure, disadvantages of the prior art regarding coupling of an external hearing device of a bone anchored hearing system with an abutment of a bone anchored hearing system may be overcome. It has been found that the coupling assembly according to the second aspect of the present disclosure significantly facilitates connecting an external hearing device with an abutment of a bone anchored hearing system, as the number of parts is limited. This also facilitates manufacturing of the coupling assembly, as fewer tolerances have to be observed with respect to other components. The coupling assembly according to the second aspect of the present disclosure thus provides a simple and cost effective solution for coupling an external hearing device with an abutment of a bone anchored hearing system.

According to a third aspect of the present disclosure, a bone anchored hearing system may comprise an implant configured to be fixated in a skull of a user and an abutment configured to be connected to the implant. The implant may comprise an osseo-integrated screw in the skull, in particular in the temporal bone, of the user. An abutment may be a connecting element to the implant of a bone anchored hearing system. The abutment may be a percutaneous abutment mounted on an implant anchored in the skull bone of a user. Preferably, the abutment may have a thread on the outside for securing the abutment inside the implant having an internal screw thread.

The bone anchored hearing system may comprise an external hearing device comprising a vibrator having a vibrator plate and a vibrator spring. The external hearing device may be configured to process an input audio signal and to provide a structure-borne acoustic signal to the user in dependence on the processed audio signal. The external hearing device may include i) an input unit such as a microphone for receiving an acoustic signal from a user's surroundings and providing a corresponding input audio signal, and/or ii) a receiving unit for electronically receiving an input audio signal. The input unit may include multiple input microphones, e.g. for providing direction dependent audio signal processing. Such directional microphone system may be adapted to (relatively) enhance a target acoustic source among a multitude of acoustic sources in the user's environment and/or to attenuate other sources (e.g. noise). Thereby, the directional system may be adapted to detect (such as adaptively detect) from which direction a particular part of the microphone signal originates. This may be achieved by using conventionally known methods.

The external hearing device may further include a signal processing unit for processing the input audio signal. The signal processing unit may include an amplifier that is adapted to apply a frequency dependent gain to the input audio signal. The signal processing unit may further be adapted to provide other relevant functionality such as compression, noise reduction, etc.

Moreover, the external hearing device may comprise an output unit including an output transducer such as a vibrator for providing a structure-borne acoustic signal. External hearing devices of bone anchored hearing systems typically use a vibrator/transducer technology to vibrate sound into the skull of a patient based on variable reluctance.

The vibrator may comprise a vibrator plate and a vibrator spring. The vibrator spring may connect the vibrator plate to a magnet arrangement of the external hearing device, thereby maintaining an essential air gap between the vibrator plate and the magnet arrangement. As soon as a supply voltage may be provided to the vibrator, causing the vibrator plate to move along a longitudinal direction, applying a vibrational force to the abutment, which in turn transfers the vibration into the skull of the patient.

The bone anchored hearing system may comprise a coupling assembly according to the second aspect of the present disclosure for coupling the external hearing device with the abutment. In particular, the vibrator of the external hearing device of the bone anchored hearing system may be coupled with the abutment of the bone anchored hearing system via the coupling assembly. The coupling of the coupling assembly according to the second aspect may be connected to the vibrator plate of the external hearing device as well as to the abutment of the bone anchored hearing system. Preferably, the coupling is connected to the external hearing device, in particular the vibrator of the external hearing device, on one side and connected to the abutment with its opposite side.

The bone anchored hearing system of the present disclosure thus allows for overcoming disadvantages of prior art bone anchored hearing systems. It has been found that with the bone anchored hearing system of the present disclosure, a comfortable hearing system is provided for a user that is particularly characterized by easy handling, secure hold and simple manufacture.

Exemplary embodiments of the first, second and/or third aspect may have one or more of the properties described below.

The at least two coupling arms of the coupling may be at least partially substantially flexible. The coupling arms being at least partially substantially flexible may allow for simple coupling and releasing of the coupling with/from the abutment. The coupling may be coupled with an abutment either with the at least two coupling arms connecting to the inside of the abutment or to the outside of the abutment.

When establishing a connection between the coupling and the abutment, the at least two partially substantially flexible coupling arms may bend outwards or inwards to either reach in or reach around the abutment. Due to the coupling arms being at least partially flexible, the coupling arms may then apply a pressure to the abutment to remain connected. Preferably, the coupling may be configured to provide a snap coupling when establishing a connection to the abutment.

The coupling may comprise at least one slot between each two coupling arms. In particular, flexibility of the at least two coupling arms of the coupling may depend on the width of at least one slot between the at least two coupling arms.

The at least two coupling arms may be configured to control axial mating and radial holding to the abutment of the bone anchored hearing system. In particular, the one-piece coupling, in particular the at least two coupling arms of the coupling, may comprise both, at least one axial mating surface and at least one radial holding surface. The at least one axial mating surface may be a surface substantially perpendicular to the insertion direction of the abutment. When coupling the abutment with the coupling, the abutment may abut against the axial mating surface with a front surface. The at least one radial holding surface may be a surface substantially parallel to the insertion direction of the abutment. When coupling the abutment with the coupling, the at least one radial holding surface may abut against a side surface of the abutment. Axial mating as well as radial holding may thus be controlled by the same one-piece component. This allows particularly allows for a simple connection between the coupling and the abutment of the bone anchored hearing system.

The coupling may be produced by injection molding. In particular, the coupling may be produced by injecting molten material into a mold. Preferably, the coupling may comprise PEEK. By producing, in particular machining, the one-piece coupling, the at least one axial mating surface and at least one radial holding surface are easier to control to tolerances.

In particular, the at least two coupling arms may be configured to at least partially establish a form-fitting and/or force-fitting connection to the abutment of the bone anchored hearing system.

Preferably, the at least two coupling arms may comprise at least one recess for at least partially establishing a form-fitting and/or a force-fitting connection to the abutment of the bone anchored hearing system. The at least one recess of the at least two coupling arms may comprise at least two surfaces, in particular at least one axial mating surface and at least one radial holding surface.

When coupling the coupling with the abutment, the abutment may abut with its front surface facing the coupling against a first surface of the recess substantially perpendicular to the direction of insertion of the abutment inside the recess of the coupling arms to control axial mating.

A second surface of the recess of the coupling arms being substantially parallel to the direction of insertion of the abutment at least partially may abut against a side surface of the abutment to control radial holding. The at least two coupling arms are thus configured to at least partially establish a form-fitting connection to the abutment of the bone anchored hearing system.

A force-fitting connection between the coupling, in particular the at least two coupling arms, and the abutment may be realized by the coupling arms being at least partially substantially flexible and thus pressing against a side surface of the abutment after the abutment has been coupled to the coupling. Moreover, a force-fitting connection between the coupling, in particular the at least two coupling arms, and the abutment may be supported by at least one biasing means for alternatively or additionally pressing the coupling arms against the abutment, in particular against a side surface of the abutment. For example, the biasing means may comprise at least one coupling spring.

The coupling may further comprise a coupling body. The at least two coupling arms may be attached to the coupling body. The coupling body may be arranged substantially on a first side of the coupling facing the external hearing device, in particular the vibrator of the external hearing device, to be attached to the coupling. The at least two coupling arms may be arranged substantially on a second side of the coupling facing the abutment to be attached to the coupling. The first side of the coupling may be opposite the second side of the coupling.

The coupling body may be configured to be attached to a vibrator of the external hearing device. In particular, the coupling body may be configured to be attached to a vibrator plate of the vibrator of the external hearing device. The vibrator plate may comprise a projection onto which the coupling may be placed. For this purpose, the coupling body may comprise an opening through which the projection of the vibrator plate fits. The one-piece coupling comprising the coupling body may thus replace the connector plate of the prior art coupling.

Preferably, the coupling body may be configured to be threaded on to a vibrator plate of the vibrator of the external hearing device. For example, the projection of the vibrator plate may comprise a thread on its outside. The coupling body may comprise a thread on the inner side of its opening. This allows for the coupling between the coupling and the vibrator plate being firm and for transmitting vibrations via the coupling to the abutment of the bone anchored hearing system.

The coupling body may be threaded on to the vibrator plate of the vibrator of the external hearing device after the vibrator plate has been installed into a housing of the external hearing device. This particularly allows for a slimmer profile of the coupling assembly as well as of the external hearing device and in particular for a smaller opening in the housing of the external hearing device and possibilities to add a sealing. Preferably, a flush fit may be ensured between the housing of the external hearing device and the coupling of the coupling assembly.

The coupling assembly may further comprise a coupling screw for counteracting the force of the coupling spring such that creep in the at least two coupling arms of the coupling is prevented. In particular, the coupling screw may prevent the coupling arms from bending inwards due to the spring force applied by the coupling spring. However, it still allows the coupling arms to flex outwards when attaching the coupling on an abutment.

The coupling screw of the coupling assembly may be attached to the coupling. In particular, the coupling screw may be attached to the coupling and also to the vibrator plate of the vibrator of the external hearing device. The coupling screw may have a thread on its outside surface and may be threaded inside a recess of a projection of the vibrator plate. The coupling screw may thus strengthen the coupling between the vibrator of the external hearing device and the coupling of the coupling assembly.

The connection between the at least two coupling arms of the coupling and the abutment of the bone anchored hearing system may be configured at least partially form-fitting and/or force-fitting. For this purpose, the at least two coupling arms may comprise at least one recess which may comprise at least two surfaces, in particular at least one axial mating surface against which the abutment rests with a front surface and at least one radial holding surface against which the abutment rests with a side surface.

A force-fitting connection between the coupling, in particular the at least two coupling arms, and the abutment may be realized by the coupling arms, in particular the at least one axial mating surface of the at least two coupling arms, pressing against a side surface of the abutment. A force-fitting connection between the coupling, in particular the at least two coupling arms, and the abutment may be realized by at least one biasing means for alternatively or additionally pressing the coupling arms against the abutment, in particular against a side surface of the abutment. For example, the biasing means may comprise at least one coupling spring.

The coupling spring of the coupling assembly may be attached to the at least two coupling arms of the coupling for applying a force on the at least two coupling arms of the coupling against the abutment of the bone anchored hearing system.

The coupling screw of the coupling assembly may be attached to the coupling of the coupling assembly for counteracting the force of the coupling spring such that creep in the at least two coupling arms of the coupling is prevented. In particular, the coupling screw may comprise a screw head which counteracts the force of the coupling spring. For example, while the coupling spring may press against the at least two coupling arms from the outside, the coupling screw, in particular a coupling crew head, may prevent the at least two coupling arms from bending inwards due to the spring force. The coupling screw may still allow the coupling spring, in particular the arms of the coupling spring, to flex outwards when attaching the coupling to an abutment.

The coupling, in particular the coupling body, of the coupling assembly may be attached to the vibrator of the external hearing device of the bone anchored hearing system. Preferably, the coupling, in particular the coupling body, of the coupling assembly may be threaded on to the vibrator plate of the vibrator of the external hearing device. As a result, the coupling may replace the prior art connection plate, simplifying the fabrication and installation of a coupling assembly for a bone anchored hearing system.

Optionally, the coupling screw of the coupling assembly may be attached to the vibrator of the external hearing device. In particular, the coupling screw of the coupling assembly may be threaded on to the vibrator plate of the vibrator of the external hearing device. The vibrator plate may comprise a projection with an axial opening in which the coupling screw may be received, in particular threaded. For this purpose, the coupling screw may comprise a thread on the outside. The projection of the vibrator plate, on the other hand, may comprise a thread on the inside of its opening. Both, the projection of the vibrator plate as well as the coupling screw may thus fit through an opening of the coupling body. This allows for the coupling between the coupling and the vibrator plate being firm and for transmitting vibrations via the coupling to the abutment of the bone anchored hearing system.

Further configurations and advantages of the invention will be explained in the following detailed description of some exemplary embodiments of the present invention in conjunction with the drawing.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

DETAILED DESCRIPTION

The detailed description set forth below in connection with the appended drawings is intended as a description of various configurations. The detailed description includes specific details for providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

Figure 1:
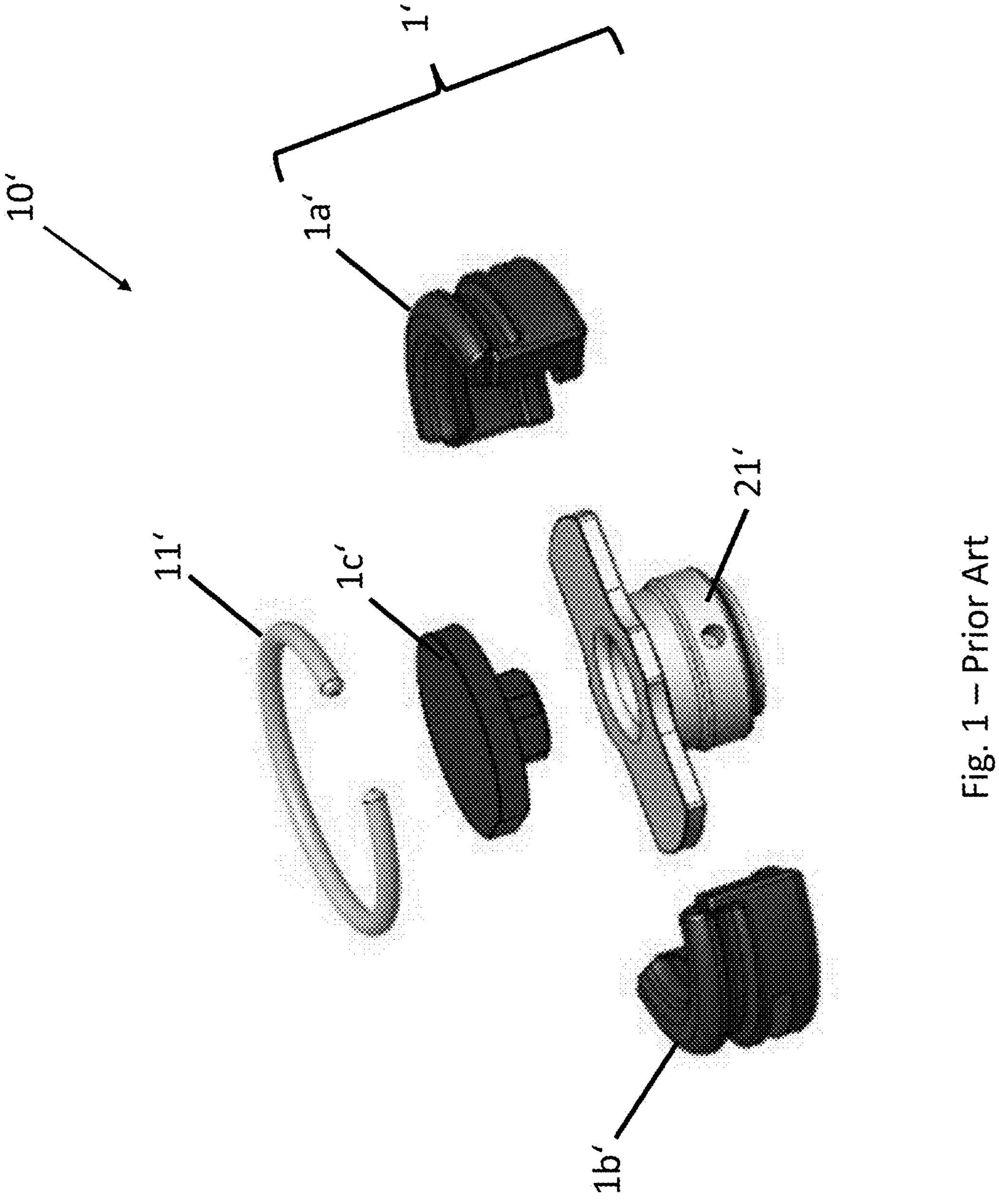
FIG. 1 schematically illustrates a coupling assembly known from the prior art.

In FIG. 1, a coupling assembly 10' known from the prior art is presented. The coupling 1' of the known coupling assembly 10' comprises left and right coupling shoes 1*a*', 1*b*' as well as a coupling plug 1*c*'. The coupling assembly 10' further comprises a coupling spring 11' configured as a C-clip metal spring. The left and right coupling shoes 1*a*', 1*b*' have to be placed in the right order on to a connector plate 21' of a vibrator of an external hearing device (not shown) of a bone anchored hearing system and the held together tightly with the coupling spring 11'. The connector plate 21' is inserted from the inside of the hearing device, which results in a large cut out in the hearing device housing (not shown) which makes sealing between the vibrator and the housing difficult. On top of that, the plurality of components comprising the coupling creates complex and sensitive tolerance chains for critical interfaces, which in turn requires difficult and expensive production control.

Figure 2:
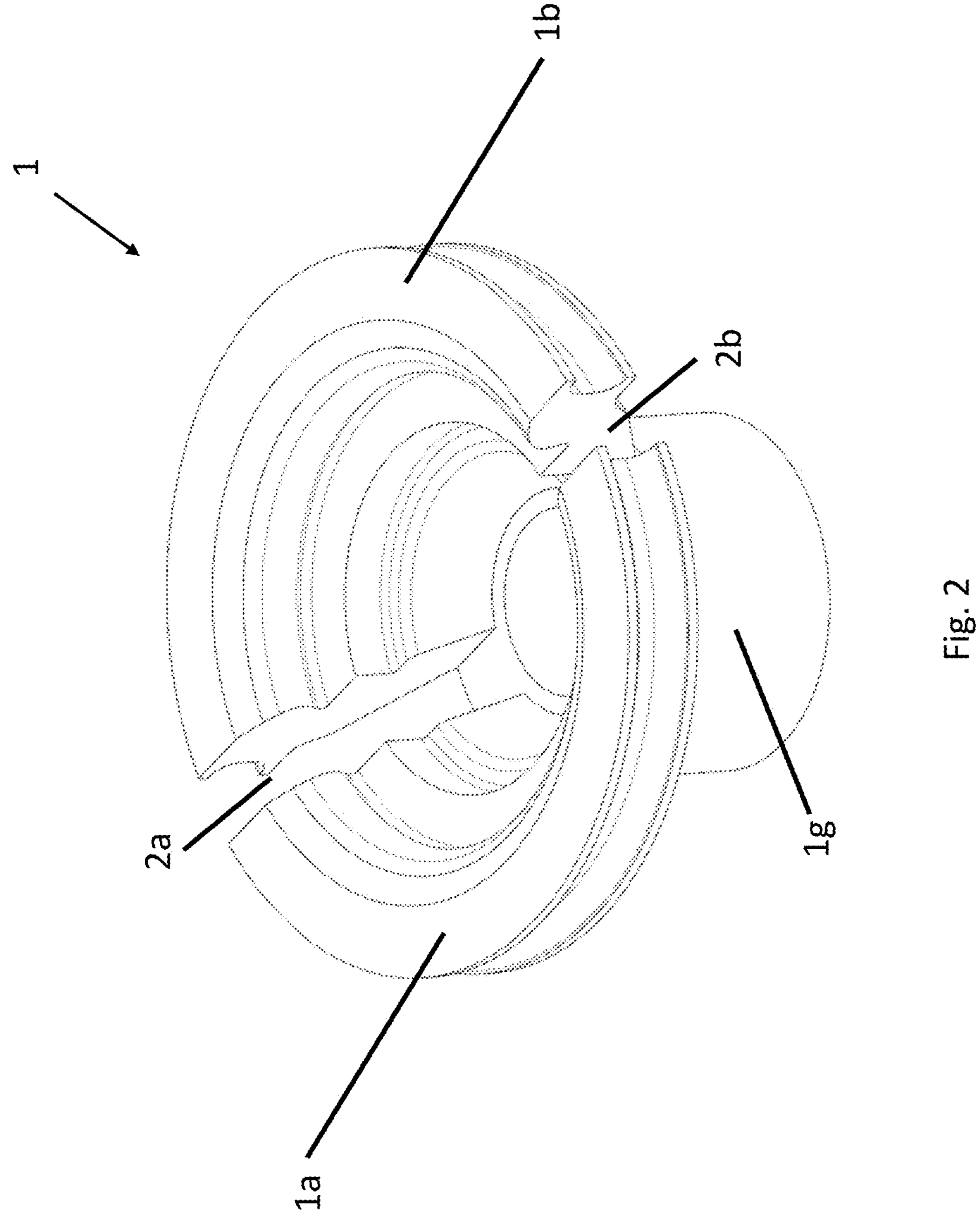
FIG. 2 schematically illustrates a first embodiment of a coupling according to the first aspect of the present disclosure.

In FIG. 2, a one-piece coupling 1 is shown which comprises two coupling arms 1*a*, 1*b* and a coupling body 1*g*. The coupling 1 thus combines the separate parts of the coupling 1' known from the prior art, namely the coupling shoes, the coupling plug as well as the connector plate, in a one-piece coupling 1. The coupling arms 1*a*, 1*b* are attached to the coupling body 1*g* and separated from each other by means of two slots 2*a*, 2*b* between the coupling arms 1*a*, 1*b*. The slots 2*a*, 2*b* allow for the coupling arms 1*a*, 1*b* being at least partially flexible. When coupled to an abutment (not shown) of a bone anchored hearing system, the coupling arms 1*a*, 1*b* may bend outward to engage the abutment. Due to the coupling arms 1*a*, 1*b* being at least partially flexible, the coupling arms 1*a*, 1*b* may then apply pressure to the abutment to remain connected.

Figures 3A, 3B:
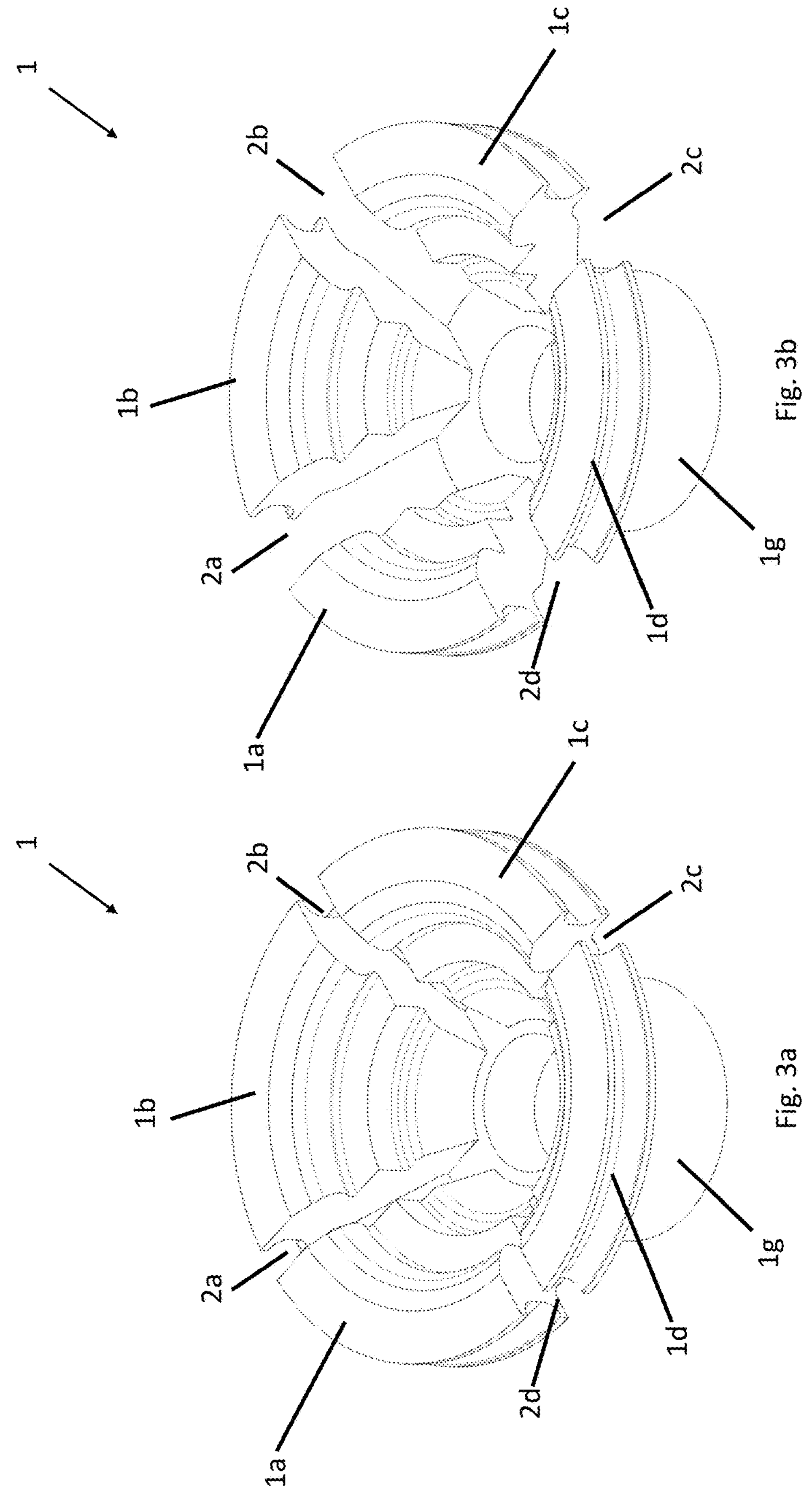
FIG. 3*a, b* schematically illustrate a second and a third embodiment of a coupling according to the first aspect of the present disclosure.

The same holds for the couplings 1 as shown in FIGS. 3*a* and *b*. The couplings 1 shown in FIGS. 3*a* and *b* each comprise a coupling body 1*g* and four coupling arms 1*a*, 1*b*, 1*c*, 1*d*. Slots 2*a*, 2*b*, 2*c*, 2*d* are provided between the coupling arms 1*a*, 1*b*, 1*c*, 1*d* of each coupling 1. The coupling 1 of FIG. 3*a* differs from the coupling 1 of FIG. 3*b* in the slot width between the coupling arms 1*a*, 1*b*, 1*c*, 1*d*. The slots 2*a*, 2*b*, 2*c*, 2*d* of the coupling 1 as shown in FIG. 3*b* have a greater width than the slots 2*a*, 2*b*, 2*c*, 2*d* of the coupling 1 as shown in FIG. 3*a*. The slot width has an impact on the flexibility of the coupling arms 1*a*, 1*b*, 1*c*, 1*d*. Due to greater slot width and thus the greater distance between the coupling arms 1*a*, 1*b*, 1*c*, 1*d* of the coupling 1 as shown in FIG. 3*b*, these the coupling arms 1*a*, 1*b*, 1*c*, 1*d* are more flexible than the coupling arms 1*a*, 1*b*, 1*c*, 1*d* of the coupling 1 as shown in FIG. 3*a*.

Figure 4:
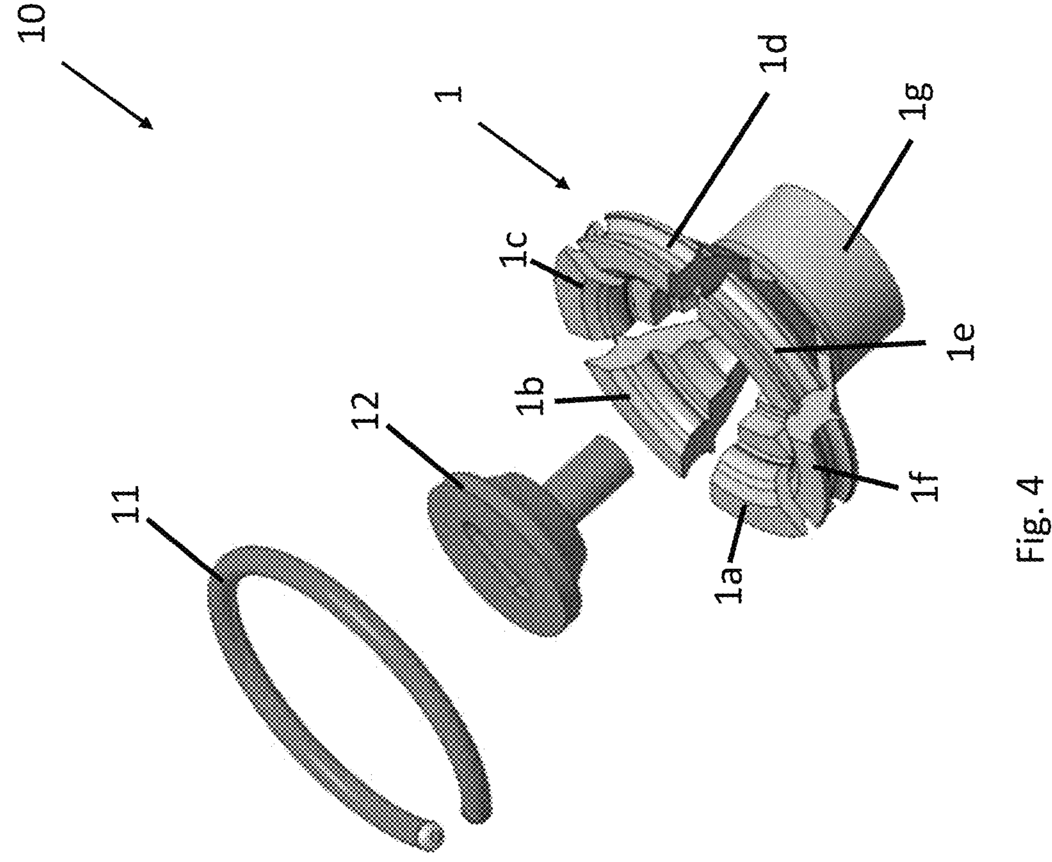
FIG. 4 schematically illustrates a first embodiment of a coupling assembly according to the second aspect of the present disclosure.

In FIG. 4, a coupling assembly 10 comprising a coupling 1, a coupling spring 11 and a coupling screw 12 is illustrated. The coupling 1 comprises six coupling arms 1*a*, 1*b*, 1*c*, 1*d*, 1*e*, 1*f*. The coupling spring 11 is a C-clip metal spring and configured to be attached to the coupling arms 1*a*, 1*b*, 1*c*, 1*d*, 1*e*, 1*f* by at least partially embracing the coupling arms 1*a*, 1*b*, 1*c*, 1*d*, 1*e*, 1*f*. The coupling spring 11 is configured to apply a force F on the coupling arms 1*a*, 1*b*, 1*c*, 1*d*, 1*e*, 1*f* of the coupling 1 against an abutment (not shown) of a bone anchored hearing system (not shown) when establishing a connection between the coupling 1 and the abutment 30 of the bone anchored hearing system 100.

Figures 5A, 5B:
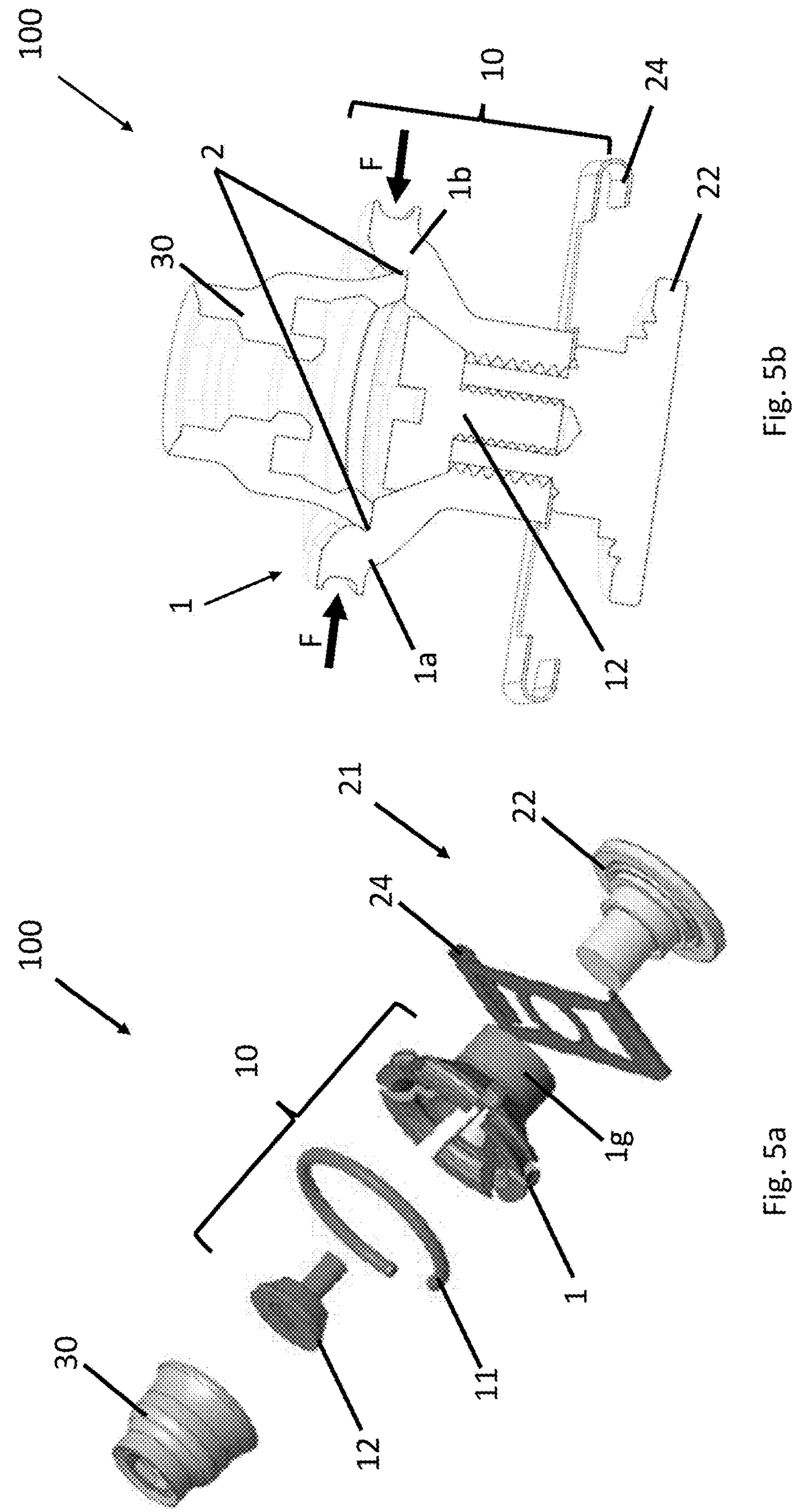
FIG. 5*a, b* schematically illustrate a first and a second embodiment of a bone anchored hearing system according to the third aspect of the present disclosure.

FIG. 5*a* shows a bone anchored hearing system 100 comprising a coupling assembly 10 with a coupling 1, a coupling spring 11 and a coupling screw 12. The bone anchored hearing system 100 further comprises an abutment 30 which is configured to be fixed onto an implant configured to be fixated in a skull of a user and a vibrator 21 of an external hearing device (not shown) of the bone anchored hearing system 100. The vibrator 21 comprises a vibrator plate 22 and a vibrator spring 24.

FIG. 5*b* illustrates a bone anchored hearing system 100 with an abutment 30, a coupling assembly 10 and a vibrator 21 in an assembled state. The vibrator plate 22 of the vibrator 21 has a thread on its outside and is threaded into the coupling 1 of the coupling assembly 10 which has a thread on the inside. The coupling arms of the coupling 1 are engaged with the abutment 30.

The coupling 1 of the coupling assembly 10 comprises at least two coupling arms 1*a*, 1 as well as a coupling body 1*g*. The coupling body 1*g* is configured to be attached to the vibrator plate 22 of the vibrator 21. To this end, the coupling body 1*g* has a thread on its inside and is thus configured to be threaded on to the vibrator plate 22 of the vibrator 21 of an external hearing device (not shown) which comprises a projection with a thread on its outside.

The at least two coupling arms 1*a*, 1*b* are configured to control axial mating and radial holding to the abutment 30 of the bone anchored hearing system 100. Both coupling arms 1*a*, 1*b* comprise a recess 2, wherein the abutment 30 with its front surface facing the coupling 1 abuts against a first surface of the recess 2 substantially perpendicular to the direction of insertion of the abutment 30 inside the recess 2 of the coupling arms 1*a*, 1*b* to control axial mating.

A second surface of the recess 2 of the coupling arms 1*a*, 1*b* being substantially parallel to the direction of insertion of the abutment 30 at least partially abuts against the side surface of the abutment 30 to control radial holding. The at least two coupling arms 1*a*, 1*b* are thus configured to at least partially establish a form-fitting connection to the abutment 30 of the bone anchored hearing system 100. Due to the flexibility of the coupling arms 1*a*, 1*b* and also the spring force F pressing the coupling arms 1*a*, 1*b* against the abutment 30 when a coupling spring (not shown) is applied, the at least two coupling arms 1*a*, 1*b* are also configured to at least partially establish a force-fitting connection to the abutment 30 of the bone anchored hearing system 100.

A coupling screw 12 of the coupling assembly 10 is attached to the coupling 1. The coupling screw 12 has a thread on its outside surface and is threaded inside a recess of a projection of the vibrator plate 22. The coupling screw 12 thus strengthens the coupling between the vibrator 21 of the external hearing device and the coupling 1 of the coupling assembly 10. At the same time, the coupling screw 12 counteracts the force of the coupling spring (not shown) such that creep in the at least two coupling arms 1*a*, 1*b* of the coupling 1 is prevented. The coupling screw 12 prevents the coupling arms 1*a*, 1*b* from bending inwards due to the spring forces F applied by the coupling spring. However, it still allows the coupling arms 1*a*, 1*b* to flex outwards when attaching the coupling 1 on an abutment 30.

Figure 6:
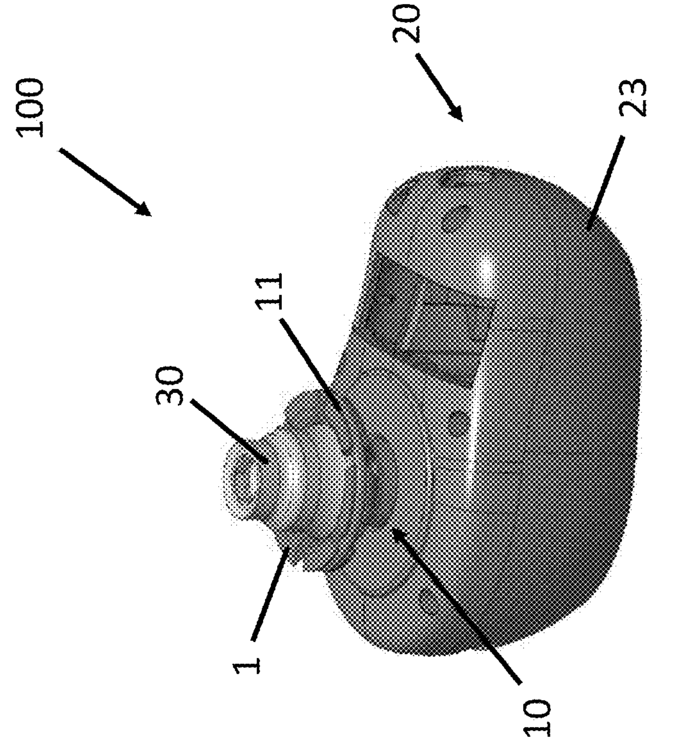
FIG. 6 schematically illustrates a third embodiment of a bone anchored hearing system according to the third aspect of the present disclosure.

In FIG. 6, a bone anchored hearing system 100 is shown which comprises an external hearing device 20 coupled with an abutment 30 via a coupling assembly 10. The external hearing device 20 comprises a vibrator (not shown) with a vibrator plate (not shown) that has been installed into the housing 23 of the external hearing device 20. The coupling 1 of the coupling assembly 10 has been threaded on to the vibrator plate after the vibrator has been installed into the housing 23 of the external hearing device 20 and thus at a later stage of the assembly process compared to the coupling assembly 10' known from the prior art. This particularly allows for a smaller opening in the housing 23 of the external hearing device 20 and for possibilities to add a sealing. The coupling 1 of the coupling assembly 10 basically covers the entire hole in the housing 23 of the external hearing device 20, thus providing a flush fit between the housing 23, in particular the top cover of the housing 23, of the external hearing device 20 and the coupling 1 of the coupling assembly 10.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element, but an intervening element may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method are not limited to the exact order stated herein, unless expressly stated otherwise.

It should be appreciated that reference throughout this specification to “one embodiment” or “an embodiment” or “an aspect” or features included as “may” means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects. Reference to an element in the singular is not intended to mean “one and only one” unless specifically so stated, but rather “one or more.” Unless specifically stated otherwise, the term “some” refers to one or more.

Accordingly, the scope should be judged in terms of the claims that follow.

The invention claimed is:

1. A coupling assembly for coupling an external hearing device with an abutment of a bone anchored hearing system, the coupling assembly comprising:

a coupling comprising at least two coupling arms for establishing a connection to the abutment of the bone anchored hearing system, wherein the coupling is configured as a one-piece coupling;

a coupling spring for applying a force on the at least two coupling arms of the coupling against the abutment of the bone anchored hearing system when establishing a connection between the coupling and the abutment of the bone anchored hearing system; and a coupling screw for counteracting the force of the coupling spring such that creep in the at least two coupling arms of the coupling is prevented.

2. The coupling assembly according to claim 1, wherein the at least two coupling arms are at least partially substantially flexible.

3. The coupling assembly according to claim 1, wherein the coupling comprises at least one slot between each two coupling arms.

4. The coupling assembly according to claim 1, wherein the at least two coupling arms are configured to control axial mating and radial holding to the abutment of the bone anchored hearing system.

5. The coupling assembly according to claim 1, wherein the at least two coupling arms are configured to at least partially establish a form-fitting and/or force-fitting connection to the abutment of the bone anchored hearing system.

6. The coupling assembly according to claim 5, wherein the at least two coupling arms comprise at least one recess for at least partially establishing a form-fitting and/or a force-fitting connection to the abutment of the bone anchored hearing system.

7. The coupling assembly according to claim 1, wherein the coupling further comprises:

a coupling body, wherein the coupling body is configured to be attached to a vibrator of the external hearing device.

8. The coupling assembly according to claim 7, wherein the coupling body is configured to be threaded on to a vibrator plate of the vibrator of the external hearing device, in particular after the vibrator plate has been installed into a housing of the external hearing device.

9. A bone anchored hearing system comprising:

an abutment configured to be connected to an implant configured to be fixated in a skull of a user;

an external hearing device comprising a vibrator having a vibrator plate and a vibrator spring; and a coupling assembly according to claim 1 for coupling the external hearing device with the abutment.

10. The bone anchored hearing system according to claim 9, wherein the connection between the at least two coupling arms of the coupling and the abutment of the bone anchored hearing system is at least partially form-fitting or force-fitting.

11. The anchored hearing system according to claim 9, wherein the coupling spring of the coupling assembly is attached to the at least two coupling arms of the coupling for applying a force on the at least two coupling arms of the coupling against the abutment of the bone anchored hearing system.

12. The bone anchored hearing system according to claim 11, wherein the coupling screw of the coupling assembly is attached to the coupling of the coupling assembly for counteracting the force of the coupling spring such that creep in the at least two coupling arms of the coupling is prevented.

13. The bone anchored hearing system according to claim 9, wherein the coupling, in particular the coupling body, and optionally the coupling screw of the coupling assembly is attached to the vibrator of the external hearing device, in particular threaded on to the vibrator plate of the vibrator of the external hearing device.

* * * * *